United States Patent [19]

Lococo

[11] 4,340,368
[45] Jul. 20, 1982

[54] DENTAL HANDPIECE OR THE LIKE

[76] Inventor: Michael P. Lococo, 4927 Victoria Ave., Niagara Falls, Ontario, Canada, L2E 1X1

[21] Appl. No.: 188,025

[22] Filed: Sep. 17, 1980

[51] Int. Cl.³ .............................................. A61C 1/02
[52] U.S. Cl. ........................................ 433/99; 433/28; 433/100; 433/85; 200/85 R; 200/157; 200/243; 200/335; 137/45; 219/242; 219/379
[58] Field of Search ............... 433/99, 98, 100, 28, 433/27, 77, 84, 85, 108; 200/85 R, DIG. 18, DIG. 35, 157, 153 R, 244, 243, 329, 335, 336, 339; 219/379, 380, 242, 246, 247, 250, 256, 257, 263, 267; 137/38, 45

[56] References Cited

U.S. PATENT DOCUMENTS

| | | | |
|---|---|---|---|
| 635,930 | 10/1899 | Harriman | 200/157 |
| 908,238 | 12/1908 | Ganser | 200/157 |
| 1,085,858 | 2/1914 | Fulton | 200/157 |
| 1,247,907 | 11/1917 | Tully | 200/85 R |
| 1,514,582 | 11/1924 | Mabey | 219/267 |
| 1,655,746 | 1/1928 | Wachtel | 200/85 R |
| 1,977,263 | 10/1934 | Campbell | 433/99 |
| 2,052,654 | 9/1936 | Ponath | 200/DIG. 18 |
| 2,134,857 | 11/1938 | Burgess | 200/157 |
| 3,430,710 | 3/1969 | Coss | 433/99 |

FOREIGN PATENT DOCUMENTS

| | | | |
|---|---|---|---|
| 1049050 | 1/1959 | Fed. Rep. of Germany | 433/98 |
| 665046 | 9/1929 | France | 219/263 |
| 897056 | 3/1945 | France | 219/267 |

Primary Examiner—Gene Mancene
Assistant Examiner—John J. Wilson
Attorney, Agent, or Firm—Stevens, Davis, Miller & Mosher

[57] ABSTRACT

A hand held power tool, particularly of the type of a dental handpiece or the like is provided with power shut-off means disposed directly within the handle. The shut-off means is mechanically connected with a suspension means for suspending the hand piece or the like power tool such that the weight of the tool shuts off power supply to the tool. In a particularly preferred embodiment, a dental handpiece is disclosed wherein the suspension means is a magnet, whereby the handpiece can be suspended on any ferromagnetic surface without having to reach to a suspension fork which, in the known devices, is itself associated with a shut-off valve. The basic idea of the invention has broad application in many different fields of technology. The advance in the art, best represented by the dental handpiece, is an added convenience of temporarily suspending the handpiece at a place remote from the suspension fork which often is inconvenient to reach, while achieving the power shut-off without having to manipulate any further control means.

23 Claims, 10 Drawing Figures

DENTAL HANDPIECE OR THE LIKE

The present invention relates to hand held power tools and in particular to a dental handpiece assembly.

The arrangement of known dental handpiece assembly in the overall apparatus is usually such that the handpiece is operatively associated with a conduit for pressurized air or fluid inclusive additional conduits for cooling liquid, etc. When not in use, a handpiece is normally suspended in a suspension fork and the weight of the handpiece causes the suspension fork to move to a shut-off position, thus deactivating the tool end of the handpiece provided with a dental burr. The suspension fork may, but need not be a part of an overall control circuit which may be operated by an additional control means such as foot operated switch or the like. The operation with dental handpiece of the above type is sometimes inconvenient as the dentist, after having completed a partial operation, sometimes has to reach far away to suspend the handpiece in the fork.

The object of the present invention is to increase the convenience of use of dental handpiece by making it possible to suspend the handpiece at locations different from the suspension fork, even though the suspension fork itself need not necessarily be eliminated. At the same time, the object of the present invention is to make sure that the state of suspending the handpiece at such different locations results in shutting off the supply of power to the tool such as dental burr or the like.

In accordance with one aspect of the present invention, the above object is solved by a dental handpiece assembly of the type including an elongate handle housing provided at one end thereof with dental burr mounting means for releasably securing a dental burr to said handle; burr drive means for rotating a burr secured in said mounting means; drive shut-off means for selectively shutting off rotary motion of a burr mounted in said mounting means; engagement means secured to said handle to form a generally integral unit therewith but being movable relative to the handle within a predetermined limits of movement, said engagement means being adapted to suspend said handle on a support and to thus move to one of said predetermined limits due to the weight of the suspended handle when the handpiece assembly is not in use; mode control means for selectively maintaining said shut-off means in one of its "on" or "off" modes; said mode control means being operatively associated with said engagement means such that the limits of movement of said engagement means correspond to the respective modes of the mode control means, said "off" mode corresponding to the limit obtained on suspension of said handle.

The basic inventive idea, however, is not limited to dental handpieces. It can be broadly defined as a hand held power tool assembly of the type including a housing unit having a tool at one end thereof and comprising handle means generally integral with said housing unit and adapted to manipulate said tool, a power source associated with power communication means communicating said source with said tool for activating the latter, and suspension engagement means at one end of said housing for engaging a support thus rendering the tool suspended when not in use, wherein said suspension engagement means is generally integral with said handle but is movable relative thereto within predetermined limits of movement, the engagement means being so arranged relative to said housing and/or said handle that on suspension of the handle, the engagement means is caused by the weight of said handle and/or said housing to reach one of said limits of movement, said engagement means being operatively associated with said power source and/or with said power communication means to discontinue supply of power to said tool when the engagement means reaches said one of said limits of movement.

In another aspect of the present invention, a hand held power tool assembly is provided of the type including a housing unit having a tool at one end thereof and handle means generally integral with said housing unit and adapted to manipulate said tool, a source of electric power associated with electric power conductor means communicating said source of electric power with said tool for activating the latter, and suspension engagement means for engaging a support thus rendering the tool suspended when not in use, wherein said suspension engagement means is generally integral with said handle but is movable relative thereto within predetermined limits of movement, the engagement means being so arranged relative to the housing and/or said handle that on suspension of the handle the engagement means is caused, by the weight of said handle and/or said housing, to reach one of said limits of movement, said engagement means being operatively associated with shut off switch means disposed within said electric power conductor means to shut off supply of power to deactivate said tool when the engagement means reaches said one of said limits of movement.

In yet another aspect of the present invention, a hand held power tool assembly is provided of the type including a housing unit having a tool at one end thereof and handle means generally integral with said housing unit and adapted to manipulate said tool, a pressurized fluid source associated with conduit means communicating said source with said tool for activating the latter, and suspension engagement means at one end of said housing, for engaging a support thus rendering the tool suspended when not in use, wherein said suspension engagement means is generally integral with said handle but is movable relative thereto within predetermined limits of movement, the engagement means being so arranged relative to said housing and/or said handle that on suspension of the handle the engagement means is caused, by the weight of said handle and/or said housing, to reach one of said limits of movement, said engagement means being operatively associated with shut-off valve means disposed in said conduit means and generally integral with said housing unit to shut off the supply of pressurized fluid medium to said tool when the engagement means reaches said one of said limits of movement.

Further features and advantages of the present invention will become more apparent from the following description of a particular application of the present invention in the art of dental handpieces and also in subsequent schematic description of slightly different arrangements utilizing the basic inventive concept, with reference to the accompanying drawings, wherein FIG. 1 is a side view of a dental piece incorporating one embodiment of the present invention;

Figures 7, 8:
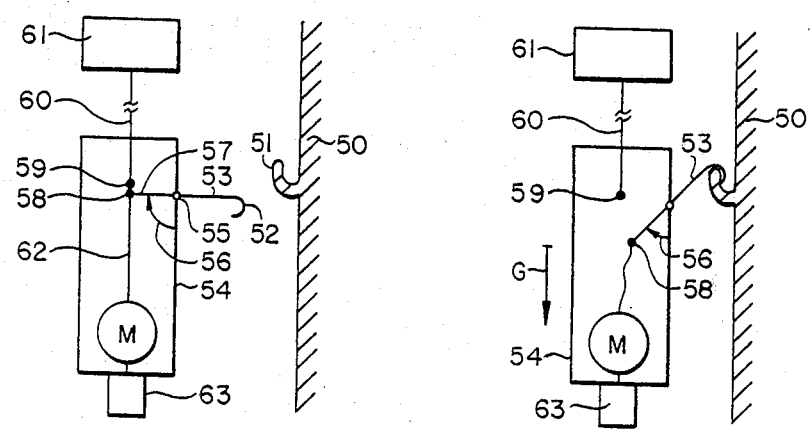
Figure 9:
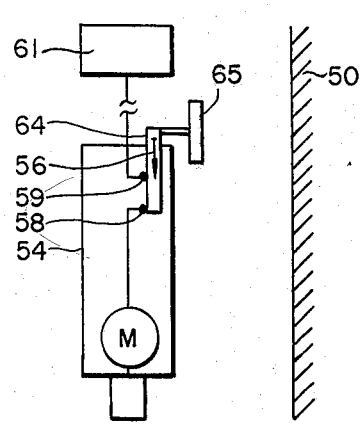
Figure 10:
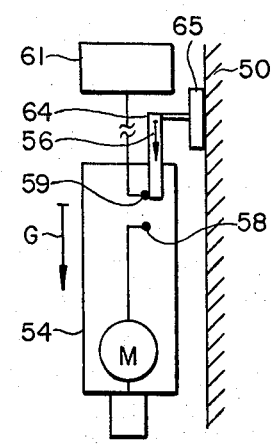

FIGS. 7 and 8 are diagrammatic representations of the operational principle of the present invention showing a power tool in a hand held position (FIG. 7) and in a suspended position (FIG. 8); and FIGS. 9 and 10 are diagrammatic representations similar to those of FIGS. 7 and 8 but showing a modified version of application of the present invention.

Turning firstly to the embodiment shown in FIGS. 1–6 and in particular to FIGS. 1–4, reference numeral 20 designates an elongate handle housing whose left-hand end is provided with a head 21 within which a turbine (not shown) is arranged for driving a dental burr, not shown, releasably secured in mounting means to protrude generally radially at 22. The described end of the handle housing 20 is well known in the art and need not be described in greater detail. Reference may be had, for instance, to Canadian Pat. No. 711,062 issued to Maurer on June 8, 1965 and to many other issued patents describing different embodiments of such handpiece.

Figure 3:
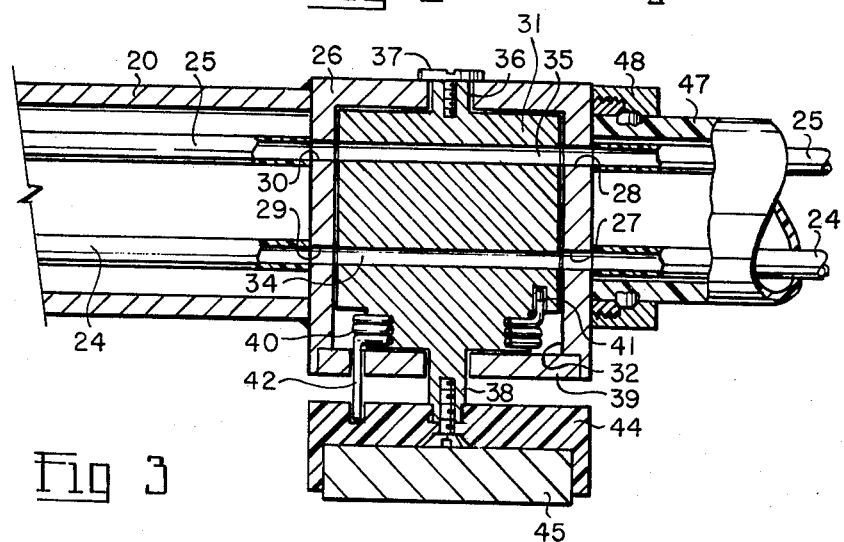
FIG. 3 is a cross sectional view on enlarged scale, taken along the line III—III of FIG. 1.

It will suffice for the purpose of understanding of the present invention, to say that within the handle 20 is disposed an air duct 23 for driving the turbine, a water coolant duct 24 and an air coolant duct 25. Integrally secured to the handle housing 20 is a valve housing 26 defining a cylindric chamber having at its inlet and discharge end appropriate channels or passages such as passages 27, 28 for communicating right-hand portions of the conduit 24, 25 with the portions of such conduits 24, 25 disposed within the handle, as best seen in FIG. 3. The discharge end of the housing 26 is provided with similar passages 29, 30, it being understood that a further passage not visible in FIG. 3 is provided to communicate the right-hand end of air duct 23 with the portion of the duct 23 disposed within the handpiece 20.

A generally cylindric valve member 31 is disposed within the cylindric chamber 32 of the valve housing and is provided with passages 33, 34 and 35 which, in an "on" position shown in FIGS. 1–4, are aligned with the respective ducts 23, 24 and 25. At one end, the valve housing is provided with a journal portion 36 provided with a screw 37 for limiting axial displacement of the valve member 31. The opposite axial end of the valve member 31 is provided with a second journal 38 which protrudes beyond an end lid 39 removably secured to the housing 26 by screws or the like (not shown for the sake of clarity).

Figure 5:
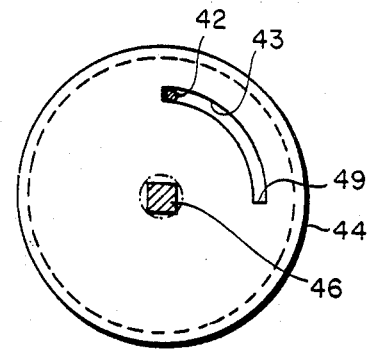
FIG. 5 is a view on line V—V of FIG. 4, partly in cross section.

The end of the valve member 31 inside the lid 39 is reduced in diameter to receive a coiled spring 40 whose one end is anchored in an axial shoulder of the valve member 31 as shown at 41. The other end of the spring 40 is provided with an axial extension 42 passing through an opening in the lid 39. The free end of the axial extension 42 engages an arcuate recess 43 of a circular tray 44 whose face turned away from the valve member 31 is provided with a magnet 45. The tray 44 is secured to the free end of the journal 38 at a squared shoulder portion 46 (FIG. 5).

Figure 4:
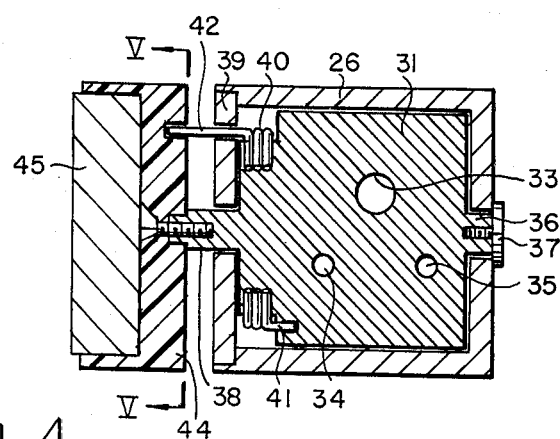
FIG. 4 is enlarged cross sectional view taken along the line IV—IV of FIG. 2.

The spring 40 is prestressed such that with the position as shown in FIGS. 3 and 4, the anchor 41 urges the valve member to assume the position aligned with the ducts 23, 24 and 25, the position being secured by engagement of the axial extension 42 at one end of the arcuate recess 43. It will be readily appreciated that in this position the conduits 23, 24 and 25 communicate with the head 21 of the handpiece. Assuming that any closures that may be included in conduits 23, 24 and 25 to the right hand side of the representations of FIGS. 1 and 2 are open and communicate with the respective sources of media, the turbine disposed within the head 21 and the accompanying means for discharge of the coolant air and coolant liquid are all operative.

Reference numeral 47 designates a flexible tube or hose enclosing the respective conduits 23, 24 and 25 and secured to the inlet portion of the valve housing 26 by an annular nut 48 in a well known fashion.

Figure 1:
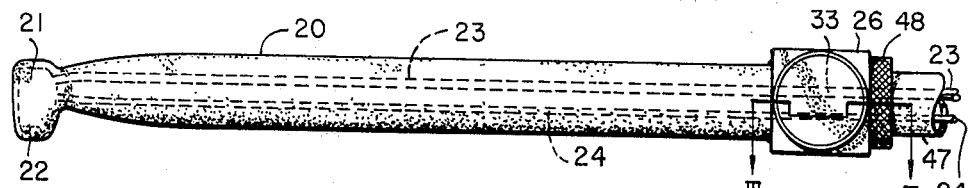
Figure 2:
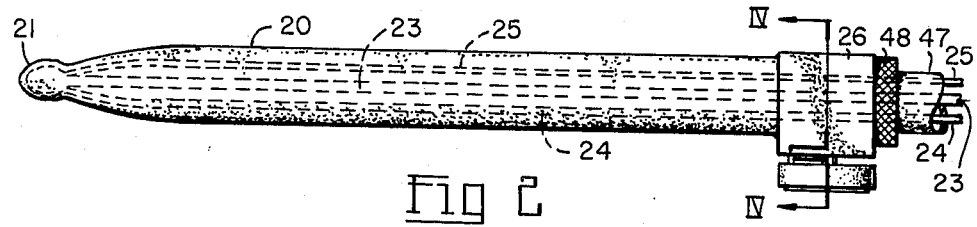
FIG. 2 is a top plan view of FIG. 1.
Figure 6:
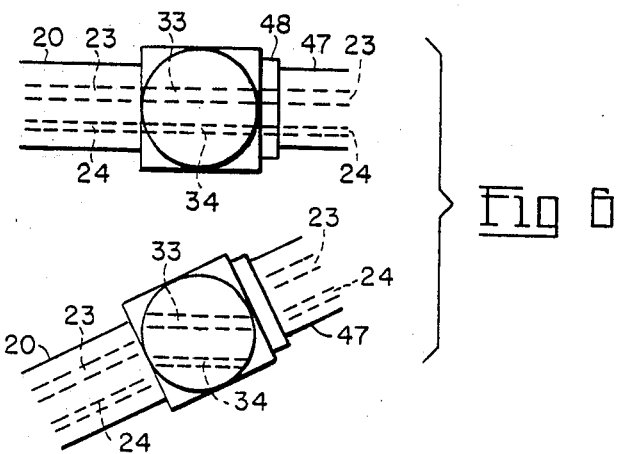
FIG. 6 is a diagrammatic indication showing the valve of handpiece of FIGS. 1 and 2 in a fully open or "on" position on top, and in an intermediate position in the bottom Figure.

Assuming now that the handpiece is held in a position wherein the axis of elongation of the handpiece 20 is generally horizontal and the axis of journals 38, 36 is also horizontal, the state is generally as shown in the upper representation of the diagram of FIG. 6, which corresponds to the state shown in FIG. 1.

If the handpiece is secured to a vertical ferromagnetic wall by adhering the surface of magnet 45 to same and releasing the hold of the handpiece 20, the weight of the handpiece 20 will cause relative rotation of the axis of elongation of handpiece 20 about the axis of the journals 38, 36. Such movement will overcome the tension of spring 40 and will cause relative movement of the tray 44 and the axial extension 42 with the result that, eventually, the axial extension 42 will engage the opposite limiting end 49 of the recess 43, in which position the handpiece shown in FIG. 2 will be suspended with its axis of elongation generally vertical. The lower part of the diagram of FIG. 6 shows the beginning of displacement to such state, at which the pivotal movement of handpiece 22 about the axis of journals 36, 38 was just started. It can be appreciated that the movement results in misalignment of channels 33, 34 relative to the respective ducts 23, 24 and, of course, also the duct 25 and the passage 35. Thus, the combination of the magnetic surface 45 with the valve arrangement as described makes it possible to not only suspend the handpiece at any plain, ferromagnetic, generally vertical surface which may be conveniently at hand but, at the same time, results in automatic shut-off of the elements disposed in the head 21.

When the handpiece is removed from its suspended state, the spring 40 forces the valve member 31 to pivot back to its "on" position as shown in FIGS. 1–5 and in the upper portion of the diagram of FIG. 6.

It will thus be appreciated that, in general terms, the magnet 45 and its associated parts form one embodiment of what may be referred to as engagement means secured to the handle. The engagement means is generally integral with the handle or handpiece 20 but is movable relative to same to effect the above closing or opening of the valve arrangement. The spring 40 and the associated axial extension 42 cooperates with the recess 43 to provide what is referred to, in general way, as "mode control means" maintaining the "shut-off means" i.e. the valve member 31, in one of its "on" or "off" modes. The limits for the respective positions, of course, are determined by the respective ends of the recess 43 in the tray 44 (FIG. 5).

As mentioned above, the basic principle of the present invention is of extreme utility in the art of dental handpieces. However, this is not to say that the basic idea cannot be used in many other arrangements of power tools, the term "power tools" in this context meaning that there is a tool at one end of a handle which is operatively connected with a source of energy, whether the source of energy be a source of electric energy, a pressurized gas or pressurized liquid or a combination thereof. The shut-off means used in the 5 different further embodiments depend, of course, on the type of power utilized in the particular tool. For instance, if the tool is an electrically heated, solder iron then the shut-off means will obviously be an electric switch. On the other hand, if the drive of the tool is effected by compressed air, then a valve, not necessarily of the type shown in FIGS. 1-6 will be preferred.

The diagrams in FIGS. 7 and 8 show one embodiment of the broad concept of the present invention. In the diagram, reference numeral 50 designates a generally vertical support surface provided with a hook 51 which is arranged for engagement by a free end hook 52 of one arm 53 of a lever pivotal relative to a handle housing 54 about a pivot 55. An arrow 56 designates the action of resilient means similar to the spring 40, and acting on the opposite arm 57 of the lever. The free end of the arm 57 is provided with connector 58 which is resiliently maintained in contact or operative communication with connector 59 of a power inlet line 60 associated with a power source 61. The connector 58 forms one end of a connection or conduit 62 which, in the embodiment shown in FIGS. 7 and 8 and also in FIGS. 9 and 10, is arranged to drive a motor M operatively associated with a tool 63 disposed at one end of the housing 54. When the tool of FIG. 7 is suspended by handling the hook 52 onto the hook 51 of the supporting surface 50, the state of the diagram of FIG. 8 is obtained. In such state, the weight G of the housing 54 and of its associated parts overcomes the resilient force 56 to thus disconnect the two connectors 58, 59, whereby the tool 63 can be deactivated solely by hanging up the tool, regardless of the particular type of suspension holding the tool on a support.

In the embodiment of FIGS. 9 and 10, another modification of the present invention is shown. Most of the elements shown in FIGS. 9 and 10 correspond to those of FIGS. 7 and 8 and are therefore marked with the same reference numerals. In FIGS. 9 and 10, however, the supporting surface 50 is of the type of a ferromagnetic surface, the lever comprising arms 53 and 57 having been substituted by a slide 64 urged by a resilient force designated by an arrow 56 to assume the position of FIG. 9. The slide 64 is effective to communicate, in the state of FIG. 9, the two connectors 58, 59. The slide 64 is movable generally parallel with the axis of elongation of the housing 54. Its end disposed outside the housing 54 is provided with a magnet 65. On adhering the magnet 65 to the surface 50, the weight G of the housing 54 gives rise to a vertical displacement of the slide 64 as the weight G overcomes the tension of resilient means 56, thus bringing the slide 64 to the state shown in FIG. 10 wherein the communication between the connectors 58 and 59 is interrupted as shown.

It will be appreciated in view of the above description and in particular in view of the diagrammatic representations of FIGS. 7-10 that many modifications of the actual application described with reference to FIGS. 1-6 may exist without departing from the scope of the present invention as described in the accompanying claims.

The embodiments of the invention in which an exclusive property or privilege is claimed are defined as follows:

1. A dental handpiece assembly of the type including:
   (a) an elongate handle provided at one end thereof with dental burr mounting means for releasably securing a dental burr to said handle;
   (b) burr drive means for rotating a burr secured in said mounting means;
   (c) drive shut-off means for selectively shutting off rotary motion of a burr mounted in said mounting means;
   (d) suspension engagement means for suspending said handle on a support and secured to said handle to form a generally integral unit therewith but being movable relative to the handle within predetermined limits of movement, said engagement means being adapted to move to one of said predetermined limits due to the weight of the suspended handle when the handpiece assembly is not in use;
   (e) mode control means for selectively maintaining said shut-off means in one of its "on" or "off" modes;
   (f) said mode control means being operatively associated with said engagement means such that the limits of movement of said engagement means corresponds to the respective modes of the mode control means, said "off" mode corresponding to the limits obtained on suspension of said handle.

2. A handpiece assembly as claimed in claim 1, wherein said engagement means is a magnet facing away from the handle housing, whereby said handpiece can be suspended from a surface of a ferromagnetic member.

3. A handpiece assembly as claimed in claim 2, wherein said shutoff means is a shut-off valve generally integral with said handle housing and disposed in a conduit for feeding a pressurized fluid to a turbine for driving said dental burr.

4. A handpiece assembly as claimed in claim 3, wherein said valve is of the type having a rotary valve member operatively associated with said engagement means and with said handle housing such as to cause the weight of said handle housing to generate pivoting of said valve member relative to said housing about a pivot axis generally perpendicular to the axis of elongation of said handle housing to thus shut off supply of the pressurized fluid to the turbine.

5. A handpiece assembly as claimed in claim 4, wherein said mode control means comprises a journal coaxial with and protruding from one axial end of said valve member and fixedly secured at its end remote from the valve member to said magnet, whereby said valve member, said journal and said magnet form a generally integral unit pivotably secured to said handle housing.

6. A handpiece assembly as claimed in claim 5, wherein said mode control means further comprises a spring and a stop means operatively associated with said valve member to resiliently urge same to an open position wherein said pressurized fluid can flow to the turbine, whereby the mode control means automatically assumes an "on" position when the handpiece is removed from a suspended state.

7. A hand held power tool assembly of the type comprising, in combination:
   (a) a housing unit having a tool at one end thereof and including handle means generally integral with said housing unit and adapted to manipulate said tool;

(b) a power source associated with power communication means communicating said source with said tool for activating the latter;

(c) suspension engagement means at one end of said housing, for engaging a support thus rendering the tool suspended when not in use;

(d) said suspension engagement means being generally integral with said handle but being movable relative thereto within predetermined limits of movement, the engagement means being so arranged relative to said housing and/or said handle that on suspension of the handle, the engagement means is caused by the weight of said handle and/or said housing to reach one of said limits of movement, said engagement means being operatively associated with said power source and/or with said power communication means to discontinue supply of power to said tool when the engagement means reaches said one of said limits of movement;

(e) reversal means of the type of a resilient member for moving said engagement means to the other limit of movement when the engagement means is disengaged from a support, to thus activate said tool; and (f) said engagement means including a magnetic surface disposed exteriorly of said housing and/or handle, whereby the power tool can be suspended on a ferromagnetic surface.

8. An assembly as claimed in claim 7, wherein said housing unit is an elongate unit, said engagement means being disposed at one end of the housing unit, the engagement means being pivotable relative to the housing unit about a pivot axis generally perpendicular to the axis of elongation of the housing unit such that on engagement of the magnetic surface with a ferromagnetic support with both the pivot axis and the axis of elongation being generally horizontal, the housing unit can tilt by gravity about said pivot axis to a shut-off position wherein the axis of elongation of the housing unit is generally vertical or sloped.

9. An assembly as claimed in claim 7 or claim 8 wherein said suspension engagement means is disposed at that end of the housing unit which is remote from said tool.

10. An assembly as claimed in claim 7, wherein said engagement means is arranged for reciprocating movement relative to the housing unit in a direction generally parallel with elongation of said housing unit.

11. An assembly as claimed in claim 7, wherein said engagement means is arranged for reciprocating movement relative to the housing unit in a direction generally parallel with elongation of said housing unit, said suspension engagement means being disposed at that end of the housing unit which is remote from said tool.

12. A hand held power tool assembly of the type including a housing unit having a tool at one end thereof and handle means generally integral with said housing unit and adapted to manipulate said tool, a pressurized fluid source associated with conduit means communicating said source with said tool for activating the latter, and suspension engagement means at one end of said housing, for engaging a support thus rendering the tool suspended when not in use, wherein said suspension engagement means is generally integral with said handle but is movable relative thereto within predetermined limits of movement, the engagement means being so arranged relative to said housing and/or said handle that on suspension of the handle the engagement means is caused, by the weight of said handle and/or said housing, to reach one of said limits of movement, said engagement means being operatively associated with shut-off valve means disposed in said conduit means and generally integral with said housing unit to shut off the supply of pressurized fluid medium to said tool when the engagement means reaches said one of said limits of movement.

13. An assembly as recited in claim 12, comprising reversal means for moving said shut-off valve means to the other limit of movement when the engagement means is disengaged from a support to thus activate said tool.

14. An assembly as claimed in claim 13, wherein the reversal means is a spring member.

15. An assembly as claimed in claim 14, wherein said engagement means includes a magnetic surface disposed exteriorly of said housing and/or handle, whereby the power tool can be suspended on a plane, generally vertical ferromagnetic surface.

16. An assembly as claimed in claim 15, wherein said housing unit is an elongate unit, said engagement means being disposed at one end of the housing unit, the engagement means being pivotable relative to the housing unit about a pivot axis generally perpendicular to the axis of elongation of the housing unit such that on engagement of the magnetic surface with a ferromagnetic support with both the pivot axis and the axis of elongation being generally horizontal, the housing unit can tilt by gravity about said pivot axis to a shut-off position wherein the axis of elongation of the housing unit is generally vertical or sloped.

17. An assembly as claimed in claim 12, 15, or 16, wherein said suspension engagement means is disposed at that end of the housing unit which is remote from said tool.

18. An assembly as claimed in claim 16, wherein said suspension element means is disposed at that end of the housing unit which is remote from said tool, said valve means being a rotary valve means whose movable valve member is fixedly secured to said engagement means, said movable valve member being pivotable relative to said housing unit about said pivot axis.

19. A hand held power tool assembly of the type comprising, in combination:

(a) a housing unit having a tool at one end thereof and handle means generally integral with said housing unit and adapted to manipulate said tool;

(b) a source of electric power associated with electric power conductor means communicating said source of electric power with said tool for activating the latter;

(c) suspension engagement means for engaging a support thus rendering the tool suspended when not in use;

(d) said suspension engagement means being generally integral with said handle but being movable relative thereto within predetermined limits of movement, the engagement means being so arranged relative to the housing and/or said handle that on suspension of the handle the engagement means is caused, by the weight of said handle and/or said housing, to reach one of said limits of movement, said engagement means being operatively associated with shut off switch means disposed within said electric power conductor means to shut off supply of power to deactivate said tool when the engagement means reaches said one of said limits of movement;

(e) reversal means of the type of a resilient spring member for moving said engagement means to the other limit of movement when the engagement means is disengaged from a support, to thus activate said tool; and (f) said engagement means including a magnetic surface disposed exteriorly of said housing and/or handle, whereby the power tool can be suspended on a ferromagnetic surface.

20. An assembly as claimed in claim 19, wherein said housing unit is an elongate unit, said engagement means being disposed at one end of the housing unit, the engagement means being pivotable relative to the housing unit about a pivot axis generally perpendicular to the axis of elongation of the housing unit such that, on engagement of the magnetic surface with a ferromagnetic support with both the pivot axis and the axis of elongation being generally horizontal, the housing unit can tilt by gravity about said pivot axis to a shut off position wherein the axis of the housing unit is generally vertical or sloped.

21. An assembly as claimed in claim 19, or 20, wherein said suspension engagement means is disposed at that end of the housing unit which is remote from said tool.

22. An assembly as claimed in claim 20, wherein said engagement means is arranged for reciprocating movement relative to the housing unit in a direction generally parallel with elongation of said housing unit.

23. An assembly as claimed in claim 20, wherein said engagement means is arranged for reciprocating movement relative to the housing unit in a direction generally parallel with elongation of said housing unit, said suspension engagement means being disposed at that end of the housing unit which is remote from said tool.

* * * * *